United States Patent [19]

Geddes et al.

[11] 4,291,699

[45] Sep. 29, 1981

[54] METHOD OF AND APPARATUS FOR AUTOMATICALLY DETECTING AND TREATING VENTRICULAR FIBRILLATION

[75] Inventors: Leslie A. Geddes; Joe D. Bourland, both of West Lafayette, Ind.; Reese S. Terry, Freeport, Tex.

[73] Assignee: Purdue Research Foundation, West Lafayette, Ind.

[21] Appl. No.: 944,369

[22] Filed: Sep. 21, 1978

[51] Int. Cl.³ ............................................. A61N 1/36
[52] U.S. Cl. ............................................. 178/419 D
[58] Field of Search ............... 128/419 D, 785, 723

[56] References Cited

U.S. PATENT DOCUMENTS

| | | | |
|---|---|---|---|
| 3,614,954 | 10/1971 | Mirowski et al. | 128/419 D |
| 3,716,059 | 2/1973 | Welborn et al. | 128/419 D |
| 4,184,493 | 1/1980 | Langer et al. | 128/419 D |
| 4,202,340 | 5/1980 | Langer et al. | 128/419 D |

OTHER PUBLICATIONS

Stratbucker et al., "Rocky Mountain Engineering Society", 1965, pp. 57–61.

*Primary Examiner*—William E. Kamm
*Attorney, Agent, or Firm*—Larry J. Palguta; John A. Young

[57] ABSTRACT

Method of and apparatus for automatic defibrillation of the cardiac ventricles of a heart wherein both the mechanical and electrical activities of the ventricles are sensed and used as operating inputs to the controls. Electrical activity is detected and measured with a pair of electrodes, and the waves of an electrocardiogram (ECG) are analyzed. When such electrical analysis indicates that ventricular fibrillation is present and persists, an electrical circuit is actuated for detecting mechanical pumping activity of the heart. Mechanical pumping activity is measured by the change in impedance between the pair of electrodes in one of the ventricles. The change of ventricular impedance is caused by the varying volume of blood contained within the ventricle and depends upon whether the ventricle is in a contracted or a relaxed state. The defibrillator is actuated only when both the mechanical and electrical activity of the ventricle indicates a need for defibrillation. Because some conditions may be encountered which closely resemble ventricular fibrillation, the defibrillator quantitatively preprograms and weighs the relative importance of the electrical and mechanical signals from the heart.

23 Claims, 10 Drawing Figures

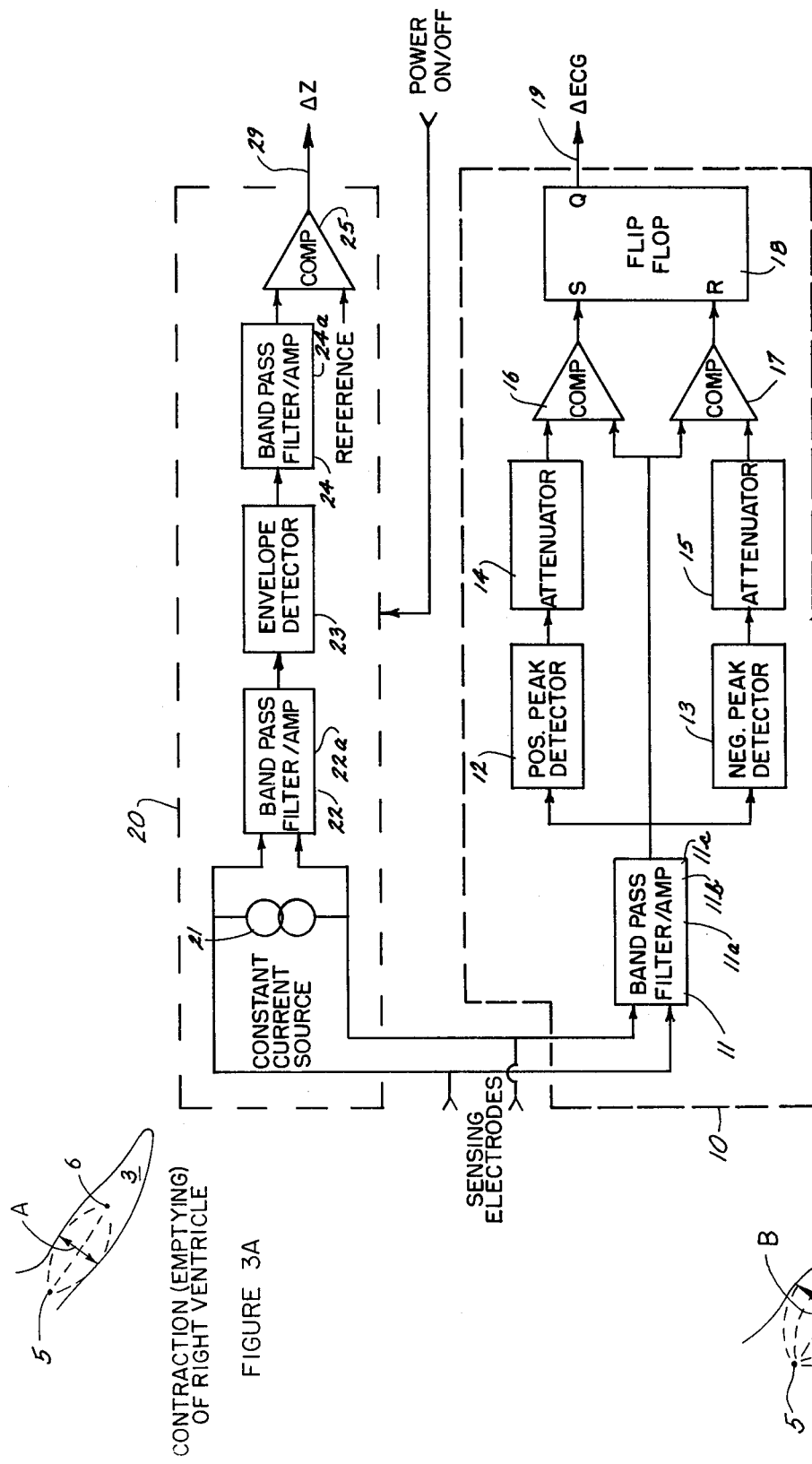

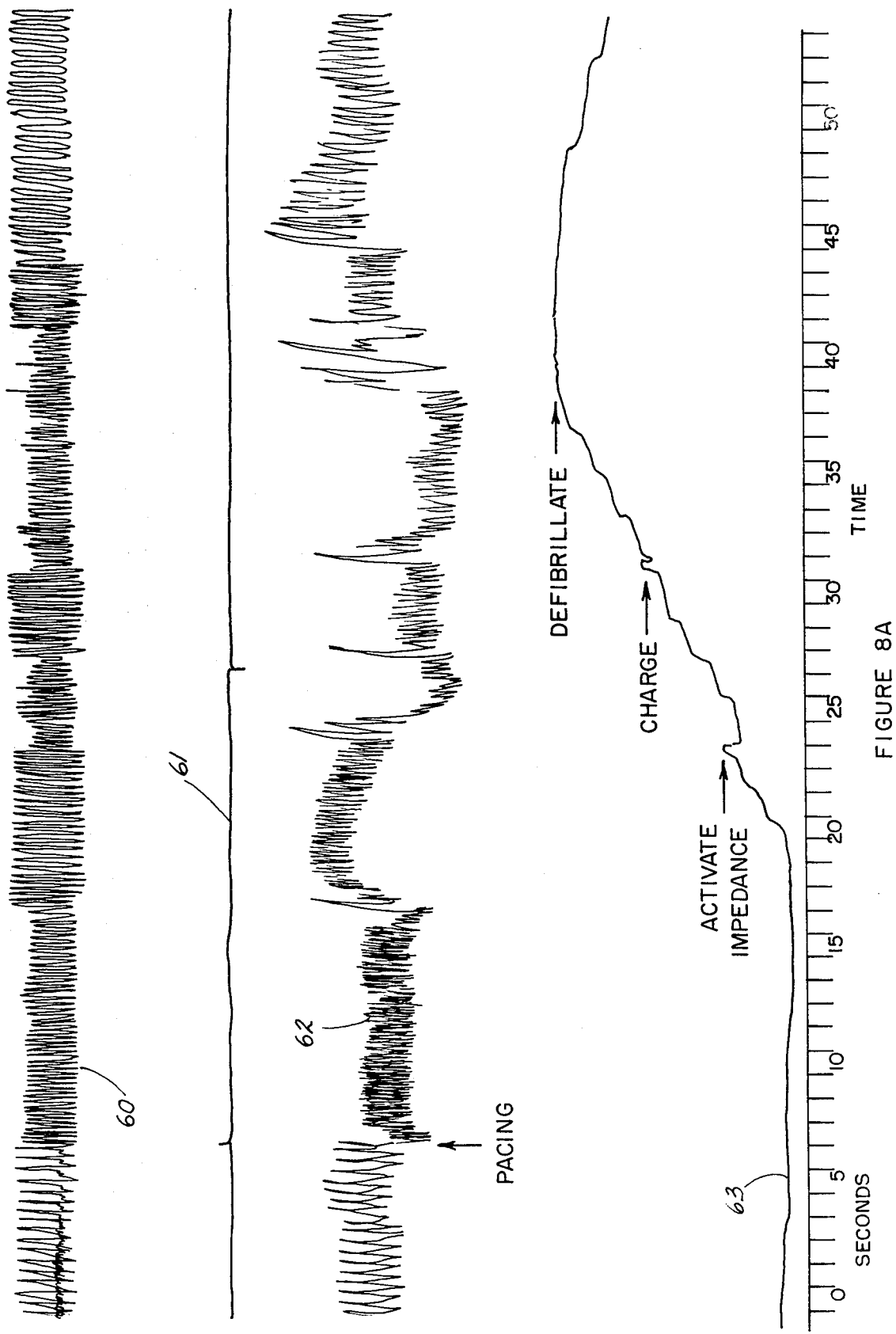

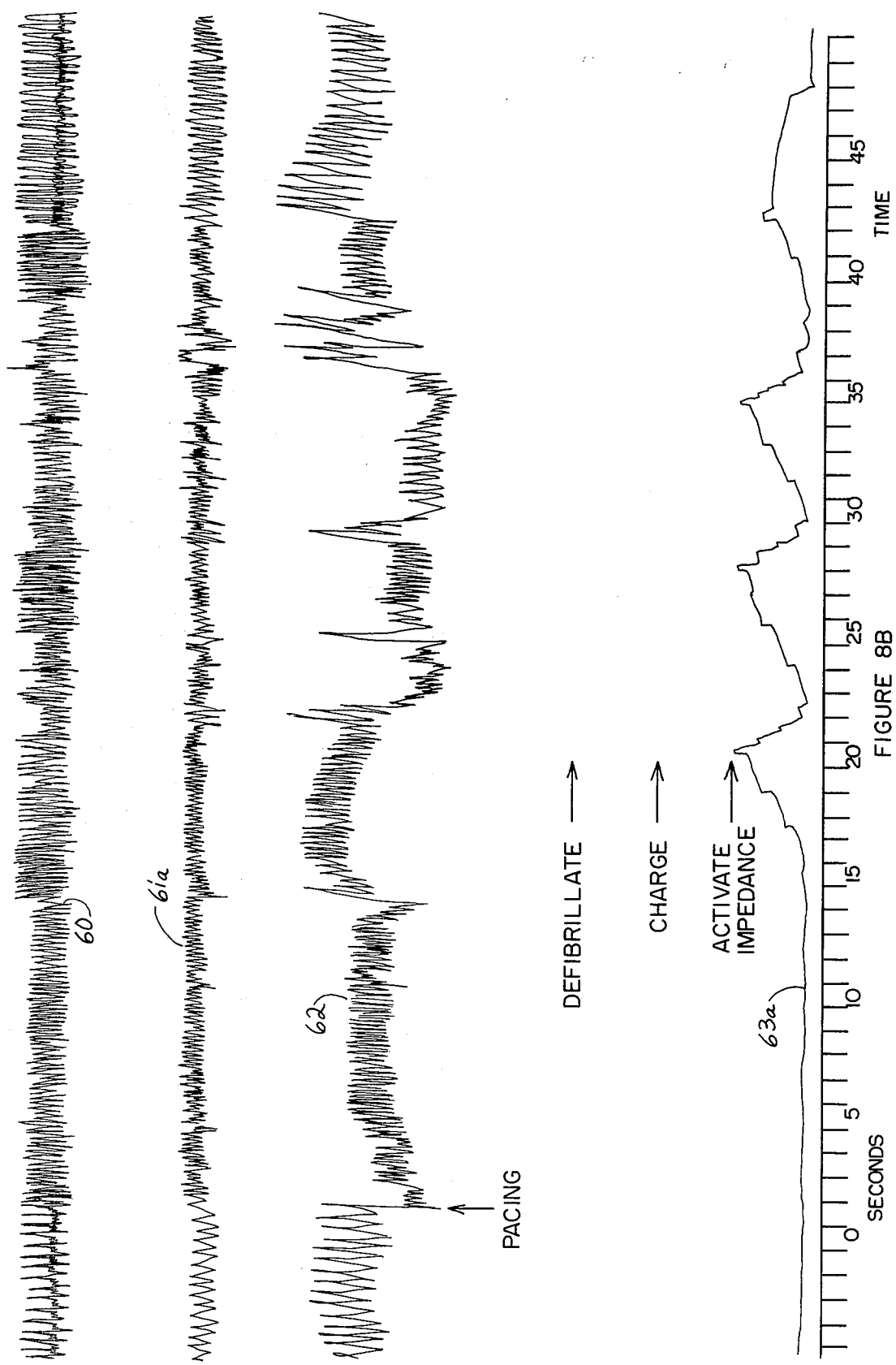

METHOD OF AND APPARATUS FOR AUTOMATICALLY DETECTING AND TREATING VENTRICULAR FIBRILLATION

BACKGROUND OF THE INVENTION

Ventricular fibrillation is a life-threatening cardiac arrhythmia resulting in the immediate loss of blood pressure. Fibrillation must be treated within minutes of its onset, or the patient may die. The only effective treatment of ventricular fibrillation is the delivery of an adequately strong electric shock to the ventricles of the heart. At present, there exists an identifiable population of patients who survive an episode of ventricular fibrillation, because of prompt therapy. Although these patients may survive their first episode of ventricular fibrillation, due to the efforts of emergency resuscitation teams, their long-term prognosis is very poor. For these patients, who are becoming more identifiable, an alternative treatment is implantation of an automatic defibrillator. A major obstacle to be overcome in the creation of such a device is development of a low power demand device and a reliable detection circuit to identify accurately ventricular fibrillation. It would, therefore, be desirable to provide an automatic implantable defibrillator incorporating a reliable detection circuit that quantitatively preprograms and weighs multiple signals received from the heart before a defibrillatory shock is delivered to the cardiac ventricles.

When functioning normally, the muscle fibers of the heart are stimulated by a wave-like electrical excitation that originates in the sino-atrial node in the right atrium. The excitation proceeds via the atrium of the heart to the ventricles. The wave-like excitation triggers the ventricular muscle fibers by causing a sequential depolarization of adjacent cells, thus creating an efficient contraction and pumping action, i.e., proper mechanical activity. Under certain conditions, e.g., partial deprivation of the oxygen supply to parts of the heart, this organized wave-like pattern is interrupted and fibrillation, a disorganized, random contraction and relaxation of the fibers of the ventricular muscle can result; this is fibrillation. During ventricular fibrillation, the muscle fibers are electrically depolarizing and repolarizing in random fashion, resulting in a chaotic twitching of the ventricular muscle, with the result that no effective pumping of blood is accomplished. By applying a suitable discharge of electrical current to the ventricular muscle fibers, it is possible to depolarize enough of the fibers at once to re-establish synchrony, thus enabling the ventricles to resume the normal rhythmic pumping.

Defibrillation as it is used today in emergency situations generally employs two electrodes placed on the chest of a patient. An electrical current is discharged through the electrodes and defibrillation of the heart is accomplished. It is well known that within minutes of the onset of ventricular fibrillation, irreversible changes start to occur in the brain and other vital organs; hence it is desirable to effect defibrillation as promptly as possible. Therefore, a reliable automatic defibrillator is desirable because of the need to terminate fibrillation promptly. It is not reasonable to expect that a trained hospital attendant will be present to aid a patient experiencing ventricular fibrillation.

Automatic cardiac defibrillator devices, which sense and analyze the electrical activity of the heart, are known in the art such as shown by U.S. Pat. No. 3,857,398. The electrical activity of the heart has typically been detected by a pair of electrodes placed in or around the heart. Such a method enables detection of an electrocardiogram (ECG) showing a record of R and T waveforms or complex indicating stages of electrical depolarization and repolarization of the ventricles of the heart. However, those devices which sense electrical activity alone have not been proven reliable, since many types of arrhythmia, i.e., a rapid beating of the heart, may mimic ventricular fibrillation and may deceive a detector monitoring only the electrical activity of the ventricles and cause it to deliver an unnecessary defibrillatory shock. With the relatively high current levels required to defibrillate the cardiac ventricles, it is imperative that no defibrillatory shock be delivered unless necessary. If the detecting system should make a false positive decision, i.e., diagnose the presence of ventricular fibrillation when it is, in fact, not present, the patient will unnecessarily experience an uncomfortable, perhaps painful and possibly harmful electric shock. If the detector should arrive at a false negative decision, i.e., fail to recognize the presence of ventricular fibrillation, the patient will probably die.

Automatic cardiac defibrillator devices which sense not only the electrical activity but also the mechanical activity of the heart are also well known in the art. Such devices have typically utilized an ECG in conjunction with one of the many methods known in the art for measurement of ventricular mechanical activity. Development of devices for measuring stroke volume are briefly discussed in an article by Geddes et al. titled "Continuous Measurement of Ventricular Stroke Volume by Electrical Impedance," (pages 118-131) appearing in the April-June 1966, Cardiovascular Research Center Bulletin published by Baylor University College of Medicine.

The electrical impedance method of measuring ventricular stroke volume has been recognized for a number of years as an effective method of instantaneously detecting mechanical pumping activity of the heart. It is well known that the resistance of a conductor depends upon the resistivity of its component material, and varies with the length, and inversely with the cross-sectional area. If the length is kept constant and the amount of conducting material between a pair of electrodes is varied, the resistance varies accordingly. Since the apex-base length of the heart remains substantially constant during systole, the resistance measured between a pair of electrodes inserted into the base and apex of a ventricle varies inversely with cross-sectional area. Further, since the conductivity of the conductive material (blood) is more than five times that of cardiac muscle, the majority of the current between the pair of electrodes is confined to the blood within the ventricle. Thus a decrease in diameter during systole decreases the cross-sectional area of the blood between the electrodes and increases the resistance measured between the electrodes inserted into the cavity at the apex and base of the heart. The blood in the ventricle constitutes, therefore, a conductor of irregular and changing shape, establishing a definite relationship between the changes in impedance and in volume during a cardiac cycle. A further understanding of the continuous measurement of ventricular stroke volume by electrical impedance is contained in the above article, which is hereby incorporated herein by reference.

Workers in the field have utilized and combined the teachings described in the article with the circuitry of an ECG for automatically detecting fibrillation. Heilman et al., U.S. Pat. No. 4,030,509, issuing June 21, 1977, also describe the placing of base and apex electrodes around portions of the heart for discharging energy. The use of an electrode covering the apex of the heart in combination with a superior vena cava catheter electrode is also described in the literature. All of the devices for measuring ventricular stroke volume by electrical impedance have required either a thoracotomy or a laparotomy. In either procedure the heart itself must be surgically exposed.

Pressure transducers attached to a catheter introduced into the heart via the superior vena cava have been employed for measuring cardiac mechanical activity, but such transducers have proven susceptible to mechanical failure and to premature disintegration during the high-current levels delivered for defibrillation. It would, therefore, be desirable to employ a single catheter implantable in the right ventricle of a heart by insertion through a superficial vein, or the superior vena cava, in the right atrium thereby decreasing surgical risk and trauma to the patient and having a plurality of electrodes for detecting and measuring ECG signals, for detecting and measuring ventricular stroke volume by electrical impedance, and for discharging a defibrillatory shock to the heart.

SUMMARY OF THE INVENTION

The present invention relates generally to cardiac defibrillators and, more particularly, to an automatic defibrillator of the type wherein both the mechanical and electrical activity of a heart are sensed and used to control the delivery of a defibrillating shock to the heart and to a method of automatically defibrillating the cardiac ventricles.

Briefly, the present invention relates to a method of and apparatus for automatic cardiac defibrillation wherein both electrical and mechanical activity of the ventricles of the heart are measured with the mechanical activity or absence thereof being sensed only at such time when the electrical activity sensor indicates possible presence of a fibrillatory condition in the ventricular myocardium. A catheter having a pair of electrodes on the distal portion thereof is insertable into the right ventricle of a heart. A third electrode located on the catheter lies in the superior vena cava. Leads from the pair of electrodes on the catheter communicate with either an implantable defibrillator control unit or an extracorporeal unit containing electrical circuits for sensing electrical R-wave activity, i.e., the electrical signal (ECG) of the ventricles and, upon command, for sensing the existing impedance between the pair of electrodes in the right ventricle thereby sensing mechanical pumping activity. The ECG and impedance circuits generate output voltages which are fed into a logic control circuit that commands the defibrillator to generate a defibrillatory shock when both mechanical and electrical activity sensors indicate the presence of a fibrillatory condition. Part of the logic control circuit includes a missing-pulse detector which delays actuation of the mechanical activity sensor until the electrical signals indicate critical fibrillatory activity of a predetermined character and extent, thus reducing the power requirement for the device. One of the important features of the present invention is to preclude continuous sensing by the mechanical activity sensor because of its relatively increased power requirements, substituting instead a "power on" which selectively commences and terminates heart surveilance by the mechanical activity sensor, limiting such activities to intermittant surveilance and thus obviating increased power demands which would otherwise be required. The device is readily usable for ambulatory surveilance and for implantation. The defibrillating shock is delivered between the third electrode in the superior vena cava and the pair of electrodes in the right ventricle, the pair of electrodes being electrically connected during defibrillation. The third electrode in the superior vena cava can be replaced by an electrode located elsewhere within the body. In fact, the metal case of the automatic defibrillator can constitute this electrode. An important feature of the present invention is the implantation of ECG and impedance sensors within the right ventricle in order to obtain more reliable information, which is relatively free from extraneous signals derived, for example, from respiration, skeletal muscular contractions, and other spurious signals which can be sensed as inadvertent signals.

Accordingly, an object of the present invention is to provide an automatic cardiac defibrillator wherein both the mechanical and electrical activity of the heart are quantitatively measured and utilized to trigger defibrillation and a method of defibrillating the cardiac ventricles.

Another object of the present invention is to provide a cardiac defibrillator having a more reliable detection circuit for detecting ventricular mechanical activity than currently available and to a method of preprogramming an ECG signal with an impedance signal representing mechanical activity.

Another object of the present invention is to provide a cardiac defibrillator with a ventricular mechanical activity sensor having a pair of spaced electrodes suspended in a ventricle of the heart for measuring stroke volume.

Another object of the present invention is to provide a cardiac defibrillator having a combination ventricular electrical and mechanical activity sensor of simplified construction to facilitate implantation thereof.

Another object of the present invention is to provide a cardiac defibrillator with a catheter extending into the superior vena cava and into the right ventricle of the heart and having a pair of electrodes in the ventricle and a third electrode in the vena cava and a method for sensing electrical (ECG) and mechanical (pumping) activities with a pair of electrodes and for connecting or shorting the pair of electrodes when criteria delivered to an accumulator circuit is accepted and delivering a defibrillatory shock to the heart through the pair of shorted electrodes and the third electrode.

Another object of the present invention is to provide a cardiac defibrillator wherein the mechanical pumping activity of the heart is sensed by measuring changes in electrical impedance, between a pair of electrodes immersed in the blood contained in one of the ventricles of the heart.

Another object of the present invention is to provide a cardiac defibrillator having a control member in which the criteria for detecting ventricular fibrillation can be digitally preprogrammed.

Still another object of the present invention is to provide an automatic implantable cardiac defibrillator wherein the impedance sensor for mechanical activity is only actuated when the electrical (ECG) activity sensor quantitatively indicates the possible presence of a fibrillatory condition, thus resulting in lower power usage by the device and consequent longer battery life of an implantable defibrillator.

Further objects and advantages of the present invention will become apparent as the following description proceeds, and the features of novelty characterizing the invention will be pointed out with particularity in the claims annexed to and forming a part of this specification.

BRIEF DESCRIPTION OF THE DRAWINGS

For a better understanding of the present invention, reference may be had to the accompanying drawings wherein the same reference numerals have been applied to like parts and wherein:

FIG. 2 shows in greater detail a block diagram of the ECG and impedance analog processors shown in FIG. 1;

FIGS. 3A and 3B illustrate the mechanical pumping activity of the right ventricle during contraction and relaxation of the ventricle and the change in the cross-sectional area of the conducting material (blood) resulting in a change in impedance;

FIGS. 8A and 8B show a recording representing performance of the detection system in an animal experiment in which the detecting system falsely diagnosed a condition as being fibrillation when only the ECG was analyzed, but correctly distinguished the condition from fibrillation when both the electrical and mechanical signals properly programmed and weighted were available to the detection system.

DESCRIPTION OF THE PREFERRED EMBODIMENT

Figure 1:
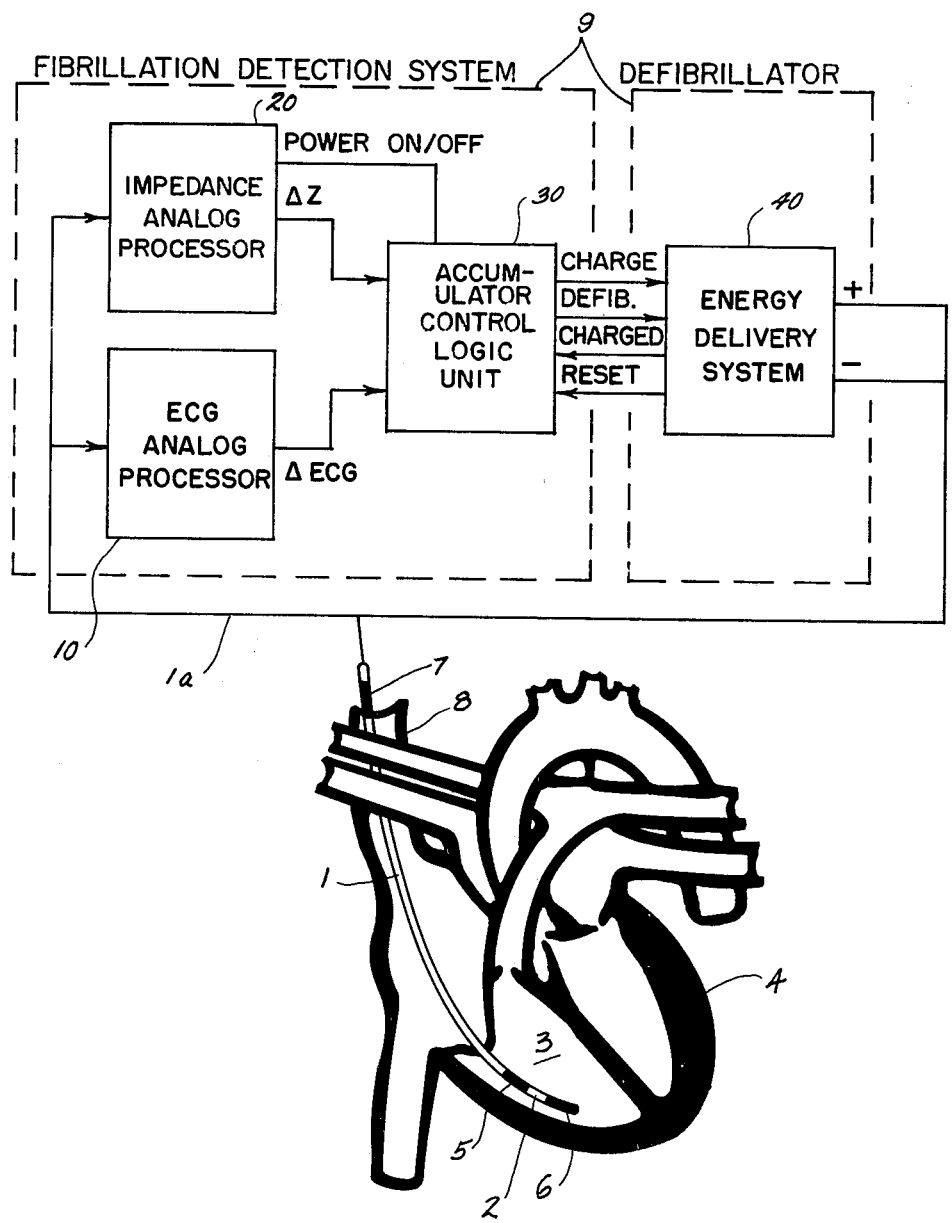
FIG. 1 shows a block diagram of an automatic defibrillator electrically connected to a catheter having a pair of electrodes implanted in the heart and a third electrode located in the superior vena cava, the catheter electrodes being operatively connected to the overall logic circuitry of the fibrillation detection system and defibrillator.

Referring now to the drawings and, more particularly to FIG. 1, a catheter 1 is shown with the distal portion 2 contained within the right ventricle 3 of the heart 4 and having a pair of sensing electrodes 5, 6 on the distal portion 2. A third electrode 7 is located on the catheter such that, when the distal portion 2 of the catheter 1 is inserted into the heart 4, the third electrode 7 will be located in the superior vena cava 8. In accord with the present invention, sensing both electrical and mechanical activities by locating the pair of electrodes 5, 6 on the catheter 1 in the right ventricle 3 does not require a thoracotomy and, when the pair of electrodes 5, 6 are shorted and employed in conjunction with the third electrode 7, defibrillation with a low intensity electrical shock is achieved. It constitutes an important feature of the present invention that the same electrodes which are disposed by the catheter in the manner described, provide a much more reliable signal of the condition of the heart than in previous devices which relied upon electrodes exterior of the heart and exterior of the ventricle cavity. Moreover, the device, disposed as it is within the heart, is efficient in deliverance of a defibrillation shock to the ventricles.

As shown in FIG. 1, there is illustrated an automatic defibrillator 9 consisting of two major blocks of electronic circuitry: a detection system 10, 20 and 30 that utilizes both the electrical and mechanical activity of the cardiac ventricles to confirm the presence of ventricular fibrillation; and an energy-delivery system 40 for generating the voltage and current necessary to defibrillate the ventricles. The energy-delivery system can be any defibrillator that can be connected to the automatic detection system through an appropriate logic interface. During operation of the defibrillator 9 shown in FIG. 1, electrodes 5 and 6 first sense electrical activity of the ventricles, i.e., an ECG signal, which is relayed to an ECG analog processor 10 via a lead 1a. After an output $\Delta$ECG signal has occurred continuously for a predetermined number of pulses, the missing pulse detector is disabled. Thereafter when the net number of waves which satisfy criteria for fibrillation reaches a second predetermined number, a control logic unit 30 gives a "command" signal through a power on/off line to an impedance analog processor 20. An impedance circuit of the processor then begins to measure signals, i.e., an impedance change ($\Delta$Z) across the pair of electrodes 5, 6 thereby measuring the instantaneous stroke volume or mechanical pumping activity of the right ventricle 3.

According to the present invention and, as best shown in FIG. 2, the ECG analog processor 10 contains a plurality of circuits for filtering signals that lie outside the bandwidth of the ECG signal, for establishing minimum amplitude excursion criteria for the fibrillation waves, and for providing means for tracking amplitude variations in the ECG signal. The low-pass section 11a of a band-pass filter 11 removes frequency components above that of the fibrillation waves. In particular, the low-pass section 11a attenuates the impedance signal produced by the impedance circuit. The high-pass section 11b of the band-pass filter 11 attenuates artifact signals, whose frequency components are below the spectrum of the fibrillation waves. In particular, the high-pass section 11b is effective in removing noise caused by respiration and electrode movement. The ECG signal is then amplified by an amplifier 11c. After amplification an envelope of the ECG signal is established by a pair of positive and negative peak detectors 12, 13. Transitions in the ECG signal greater than a fixed percentage, determined by a pair of attenuators 14, 15 of the peak-to-peak value of the signal, are detected by a pair of comparators 16, 17. A transition in the positive direction in the ECG signal greater than the value set by the positive attenuator 14 causes a bistable multivibrator (flip-flop) 18 to be set. A similar transition in the negative direction causes the flip-flop 18 to be reset. Thus, according to the present invention, the waveform of the ECG signal must exhibit excursions that approach the peak-to-peak value of the signal, as determined by the recent history of the signal, in order for the output signal ΔECG 19 to change states. In a normally beating heart, the ΔECG signal 19 contains one pulse per R-wave and false sensing of the T-wave of the ECG signal is avoided unless it becomes almost as large, has the same polarity and has nearly the same frequency spectrum as the R-wave. When fibrillation occurs, the ΔECG signal 19 contains one pulse for almost every fibrillation wave. The derived ΔECG signal 19 is then fed into the control logic unit 30, as shown in FIG. 1.

Referring now to the impedance analog processor 20 of the present invention, the impedance between the pair of electrodes 5, 6 is measured by passing a low amplitude, high frequency constant-current through the electrode circuit and measuring the resulting voltage drop across the pair of electrodes 5, 6. According to Ohm's Law, $V = IZ$, V is voltage across the electrodes, I is the value of current from the constant-current source and Z is the impedance between the electrodes. Since I is constant, the voltage between the pair of electrodes 5, 6 is directly proportional to the impedance between them.

Preferably in accord with the present invention, and as shown in FIG. 3, instantaneous impedance is measured across the pair of electrodes 5, 6 during the contraction and relaxation phases of the right ventricle 3. During the contraction phase, the diameter of the ventricle 3, represented schematically by line A, is smaller than the diameter during the relaxation phase, represented as line B. Thus, in the relaxed state, more blood is present in the ventricle 3, thereby providing a greater conductive volume for flow of the constant-current source through the pair of electrodes 5, 6 and, therefore, the impedance is lower than during the contracted state. In the contracted state, a lesser volume of blood in the ventricle 3 results in a smaller conductive volume between the electrodes and, therefore, a higher impedance. When normal rhythmic changes in impedance are recorded, proper contraction-relaxation cycles of the heart exist. However, if changes in impedance decrease and approach zero, as is the case during ventricular fibrillation, a cessation of the mechanical pumping activity of the heart 4 is indicated and the presence of a fibrillatory state is confirmed. Fibrillation is indicated when there is little if any change in impedance in the heart because of the failure to effect a rhymthic volumetric change in blood during successive phases of heart beat. Therefore, if there is no change or only little change of impedance because of low variation in blood volume within the ventricles, this is an accurate indicator of fibrillation. Electrical activity of the heart 4 monitored by the ECG signal will accurately indicate a suspected fibrillatory state which can then be confirmed by the lack of change or rate of change in impedance sensed by the impedance analog processor 20.

Referring again to FIG. 2 and the impedance analog processor 20, a 20 KHz square wave is generated by a constant-current source 21. The average value of the current from the current source 21 should be zero so that polarization of the pair of electrodes 5, 6 is avoided. The high-pass section 22a of the band-pass filter 22 of the impedance analog processor 20 passes the impedance-related voltage but attenuates signals with a spectrum below that of the constant-current source. In particular, the high-pass section 22a of the band-pass filter 22 attenuates the ECG signal so that the impedance analog processor 20 responds only to the mechanical activity of the ventricles of the heart 4.

Figure 4:
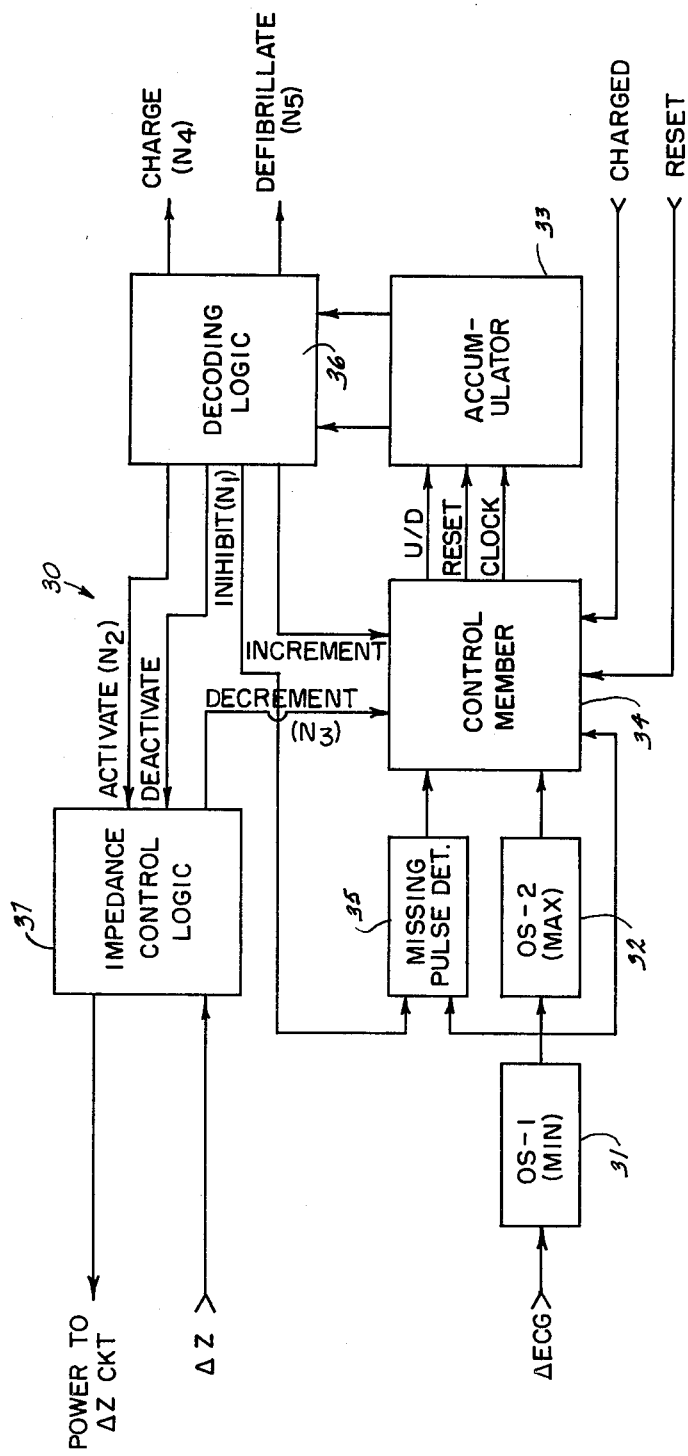
FIG. 4 shows in greater detail a block diagram of the accumulator and control logic unit with the missing-pulse detector included therein

Changes in impedance are measured by detecting changes in the amplitude of the signal measured between the pair of electrodes 5, 6, i.e., by passing the signal through an envelope detector 23 after amplification. Bandwidth of the impedance analog processor 20 is restricted to that associated with the mechanical activity of the ventricles by a band-pass filter 24. After amplification of the impedance signal corresponding to mechanical activity by an amplifier 24a, any change in impedance greater than the level set by the reference signal is detected by a comparator 25. In a normally functioning heart, the output signal ΔZ 29 from the impedance analog processor contains one pulse per ventricular contraction. The derived signal ΔZ 29 is then fed to the accumulator and control logic unit 30 shown in FIGS. 1 and 4.

The algorithms that confirm the presence of fibrillation on the basis of the ΔECG 19 signal from the ECG analog processor and the ΔZ signal 29 from the impedance analog processor are embodied in the control logic unit 30. The control logic unit also contains the means used to control the energy delivery system of the defibrillator which provides the electrical shock necessary to arrest ventricular fibrillation.

In the initial state and during normal activity of the heart, the impedance analog processor is inoperative while the ECG signal is continuously interrogated for fibrillation waves. The time interval between pulses in the signal ΔECG 19 from the ECG analog processor 10 must be within the criteria set by a pair of retriggerable monostable multivibrators, commonly known as one-shots, OS-1 and OS-2, shown in FIG. 4, as 31 and 32, respectively. Of course, other means for setting the frequency criteria for fibrillation waves could be employed. An advantage of using the retriggerable one-shots 31, 32 to set the frequency criteria for fibrillation is that the bandwidth limits are sharply defined. Transitions occurring faster than the limits set by one-shot 31 or slower than the limits set by one-shot 32 are rejected. Each wave in the ECG signal satisfying the amplitude criteria for fibrillation set by the ECG analog processor 10 and the frequency criteria set by the one-shots 31, 32 causes an accumulator 33 to increment via a central control logic member 34. Each wave in the ECG signal failing to satisfy either the amplitude criteria or frequency criteria causes the accumulator 33 to decrement via the central control logic member 34. Thus, in the absence of pulses from the impedance analog processor 20, the number in the accumulator 33 represents the net number of waves in the ECG signal that qualify as waves of fibrillation.

When the ventricles are beating normally, if the accumulator 33 contains a number greater than zero, it will be decremented by each heartbeat. In a normally beating heart, the central control logic member 34 latches the accumulator 33 at zero by inhibiting a decrement when the accumulator 33 contains zero. A missing-pulse detector 35, illustrated in FIG. 4, demands that a number N1, of successive waves in the ECG signal satisfy the fibrillation criteria. If a single wave fails to satisfy the criteria before N1 successive waves which satisfy the fibrillation criteria are accumulated, the accumulator 33 is reset to zero by the missing-pulse detector 35 via the central control logic member 34. The missing-pulse detector 35 prevents the EGC waveforms which contain two or more waves that satisfy the fibrillation criteria followed by one which does not satisfy the criteria from causing a net accumulation in the accumulator. Thus, the missing-pulse detector 35 prevents the control logic member 34 from interpreting some conditions of ventricular tachycardia as ventricular fibrillation, without having to activate the impedance analog processor 20 to make that decision. When a count of N1 is reached, the missing-pulse detector 35 is inhibited via a decoding logic member 36. The missing pulse detector 35 acts as a threshold to the accumulator by screening out fibrillation signals until a definite pattern has developed after which the detector 35 can no longer operatively reset the accumulator.

When the accumulator counts a sufficient number N2, of waves in the ECG signal which satisfy the fibrillation criteria, an impedance control logic member 37 is activated. A change in impedance satisfying the criteria for mechanical pumping causes the next N3 waves in the ECG signal to decrement the accumulator 33. Thus in accord with the present invention, the relative importance of electrical and mechanical activity can be digitally preprogrammed by selecting the decrementing factor, N3. For example, if N3=1, then electrical and mechanical events have equal importance. When N4 waves, which satisfy the criteria for ventricular fibrillation have been accumulated, charging of the energy-storage capacitor is initiated. When N5 waves have been accumulated and the energy-storage capacitor is charged, the energy delivery system or the defibrillator 40 is commanded to deliver a shock. Thereafter, the accumulator is automatically reset to zero, monitoring of the ECG signal is resumed and the impedance control logic 37 is deactivated via the decoding logic member 36.

Figure 5:
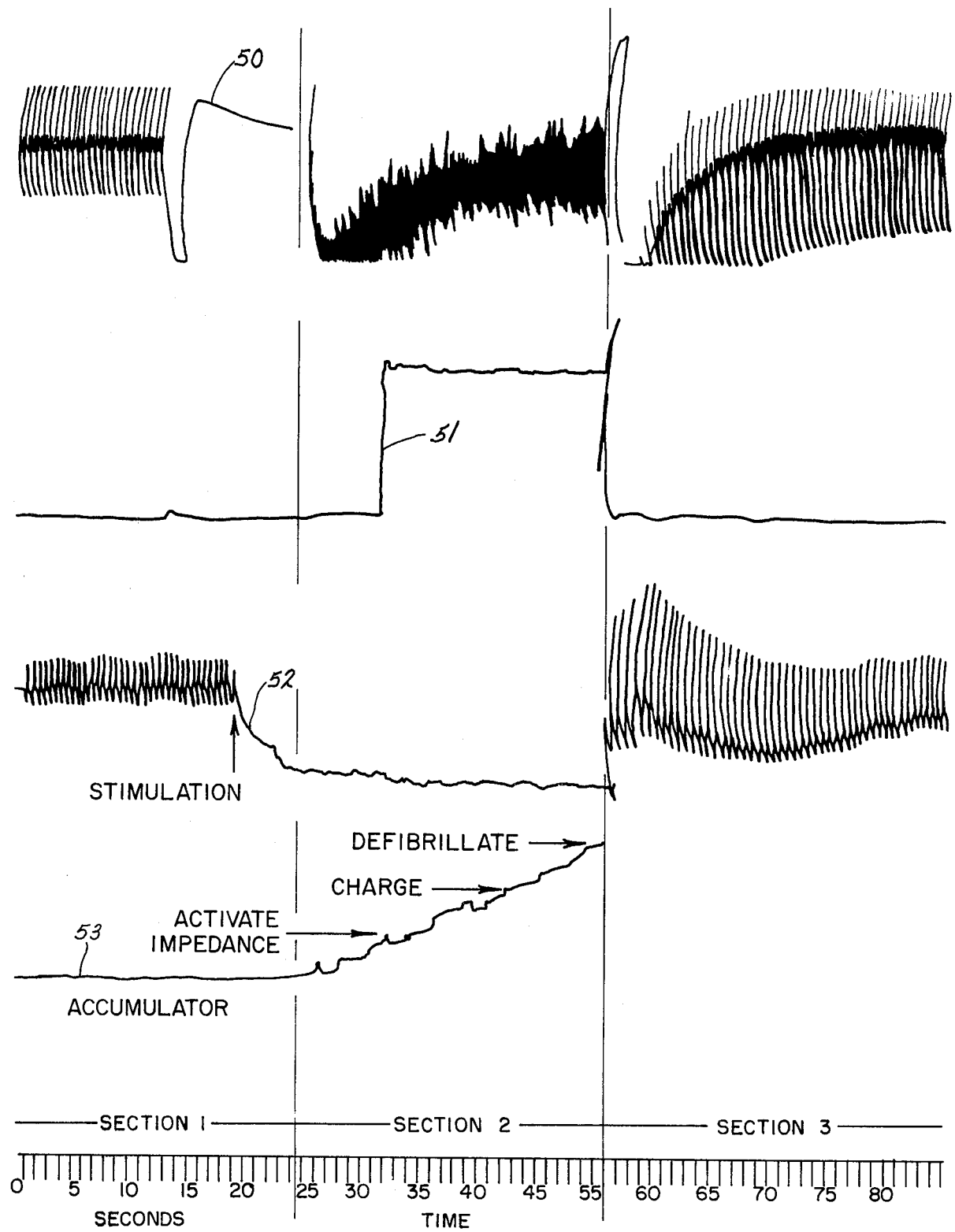
FIG. 5 shows a recording of waveforms useful in describing the functions of the components of this invention.

Operation of the automatic defibrillator 9 can be more clearly illustrated by FIG. 5, which shows plots of an R-wave complex 50 of the EGC output, an intraventricular impedance 51, a blood pressure record 52, and an accumulator record 53 obtained in animal tests utilizing the present invention. Section 1 of FIG. 5 shows the ECG signal 50, impedance signal 51, arterial pressure 52, and content record or pen excursion 53 of the accumulator for a normally functioning heart. (It should be noted that the impedance analog processor has been overridden in order to demonostrate the impedance signal obtained from a normally functioning heart.) The number contained in the accumulator unit has been displayed by connecting the accumulator unit to a not shown digital-to-analog converter. The lower limit of pen excursion 53 corresponds to zero in the converter; the upper limit of pen excursion corresponds to N5 in the accumulator.

In section 2 of FIG. 5 ventricular fibrillation has occurred, as noted by the dramatic change in the ECG signal 50, the absence of pumping signals in the impedance record 51, and the rapid decrease in arterial pressure 52. When N4 is reached in the accumulator, charging of the defibrillator energy-storage capacitor is initiated. When N5 is in the accumulator and the energy-storage capacitor is fully charged, the defibrillating shock is automatically delivered, thereby arresting fibrillation.

In section 3 of FIG. 5, restoration of pumping is achieved and the automatic defibrillator returns to the monitoring state.

A unique feature of the detecting system of the present invention relates to the ability to modify performance of the system simply by changing the mechanical-to-electrical weighting factor, $N_3$. The weighting factor, $N_3$, can be preprogrammed so that a desired decision is reached in the presence of a variety of tacyarrhythmias. For example, an inappropriate choice of the weighting factor, $N_3$, has been selected for the tacyarrhythmias illustrated in FIG. 6, and an incorrect decision is reached. However, a correct decision is reached when the weighting factor, $N_3$, is appropriately preprogrammed, illustrated in FIG. 7.

Figure 6:
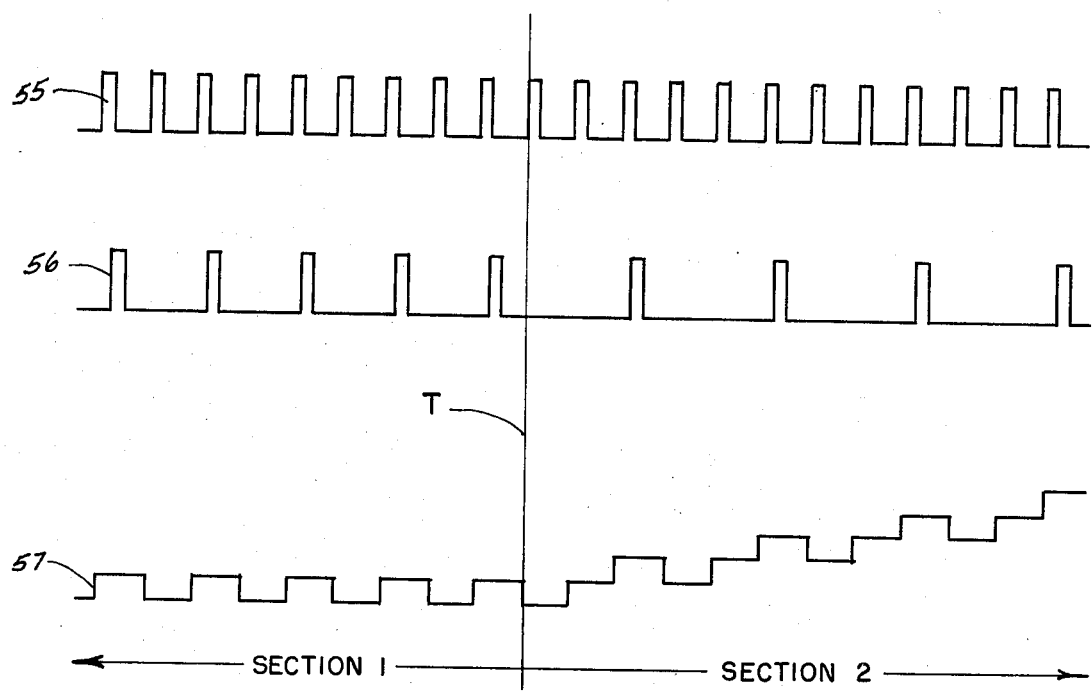
FIG. 6 illustrates the output from the analog processor in a physiological condition known as pulsus alternans, in which only every other electrical depolarization (in the ECG) is followed by a mechanical contraction and performance of the detection system, preprogrammed for equal weighing of the electrical and mechanical signals, is illustrated.

FIG. 6 shows simulated records of an output signal 55 of the ECG analog processor, $\Delta$ECG, an output signal 56 of the impedance analog processor $\Delta Z$, and a signal 57 which represents the number contained in the accumulator. Each increasing step in the accumulator signal represents an increase of one count in the accumulator.

In section 1 of FIG. 6, a cardiac condition known as pulsus alternans, in which only every other electrical depolarization is followed by a mechanical contraction, has been simulated, and the electrical and mechanical signals have been preprogrammed to have equal weighting, i.e., $N_3=1$. As indicated in the accumulator record 57, the net accumulation in this condition is zero.

In section 2 of FIG. 6, at a time T, a change in the cardiac condition occurred and every third instead of every other electrical depolarization of the ventricles causes a mechanical contraction. With $N_3=1$, a (false) decision that ventricular fibrillation exists will be reached.

Figure 7:
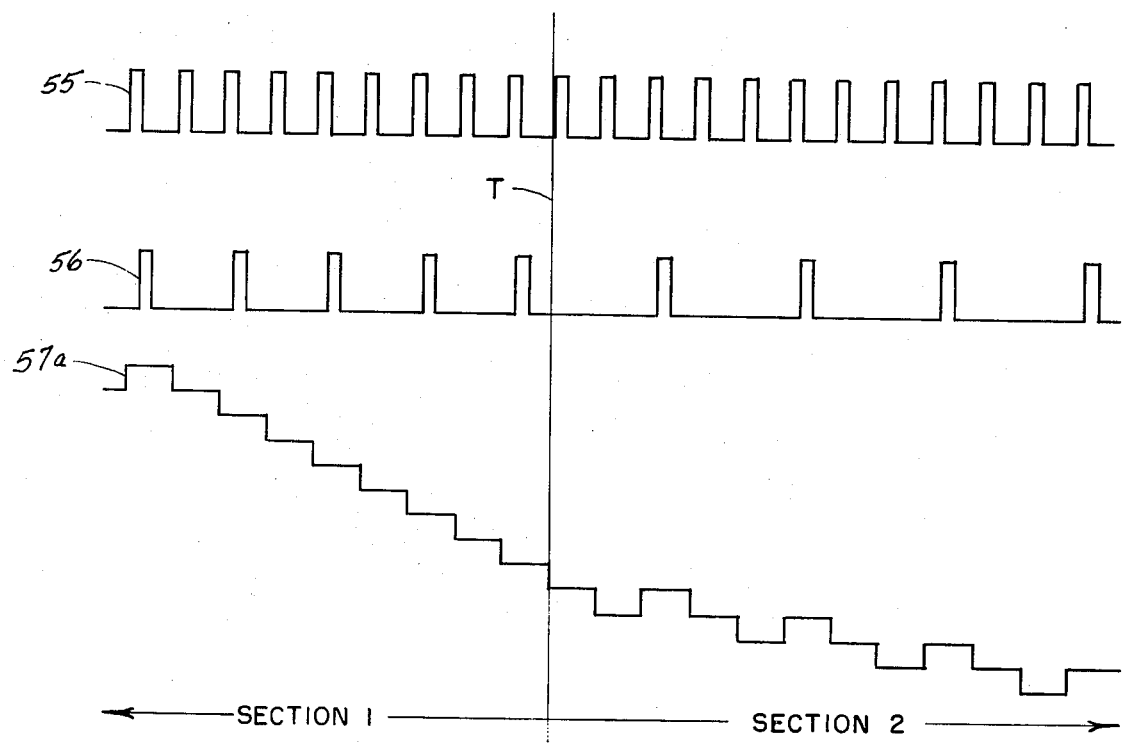
FIG. 7 shows a recording of a condition similar to that illustrated in FIG. 6; however, the detection system has been preprogrammed so that mechanical activity has twice the weight of electrical activity.

FIG. 7 illustrates performance of the detection system under the conditions of FIG. 6; however, the mechanical signal in accord with the present invention had been preprogrammed to have twice the weight of the electrical signal, i.e., $N_3=2$. The correct decision, that ventricular fibrillation does not exist, will be reached by the accumulator record 57a even when only every other or third electrical depolarization is followed by a mechanical contraction, as illustrated in sections 1 and 2 of FIG. 7.

It should be noted that, in practice of the invention, other weighting factors and algorithms for combining the electrical and mechanical activities of the heart may be employed. It is to be understood that the above examples are merely illustrative and not restrictive.

FIG. 8A shows a record of a complex arrhythmia 60 created in an animal experiment, a related impedance signal 61 that is disconnected and a related femoral artery pressure signal 62. The detection system is deprived of the information from the mechanical system, i.e., the impedance signal 61, and, as illustrated, the accumulator 63 has made the (incorrect) decision that ventricular fibrillation exists. As the accumulator increases, it activates the impedance analog processor 20, charges the capacitor of the defibrillator 40, shorts the pair of electrodes 5, 6 and automatically delivers the shock to the heart. In FIG. 8B, the mechanical activity represented by an impedance signal 61a is connected to the control logic unit 30 and the (correct) decision, that ventricular fibrillation does not exist, is reached. No unnecessary shock is delivered to a patient in this situation.

In addition to the advantages previously discussed with regard to the method of utilizing preprogramming and weighting the relationship between the intraventricular impedance and the ECG signal for detecting the loss of mechanical pumping, such a method also allows identification of a fault in the electrodes, since any electrode break will immediately produce a dramatic increase in circuit impedance. Additional circuitry can be incorporated to detect such an impedance increase and indicate electrode malfunction.

It should be appreciated that the defibrillator 9 described herein may be advantageously combined with a not shown pacemaker unit, e.g., where defibrillation is accomplished but cardiac pumping is not resumed. In such a case, pacing is necessary. Also the entire defibrillator or any portion thereof can be located either in an implantable unit or in an extracorporeal unit, as desired.

While there has been illustrated and described what is, at present, considered to be a preferred embodiment of the invention, it will be appreciated that numerous changes and modifications are likely to occur to those skilled in the art, and it is intended in the appended claims to cover all those changes and modifications which fall within the true spirit and scope of the present invention.

What is claimed as new and desired to be secured by Letters Patent of the United States is:

1. An automatic cardiac ventricular defibrillator comprising: means for sensing electrical and mechanical activity of a cardiac ventricle in the form of ECG analog signals and the impedance of the ventricle, an ECG analog processor for producing an ECG analog processor signal of a fibrillatory condition, means for communicating the sensed electrical activity to said ECG analog processor, accumulator-control-logic means for counting fibrillatory signals, means for communicating an ECG analog processor signal of a fibrillatory condition from said ECG analog processor to said accumulator-control-logic means, an impedance analog processor operatively connected to said sensing means and responsive to said accumulator-control-logic means and for developing a signal of a non-fibrillatory condition which effects a decrementing count, means for communicating an activation switching action to said impedance analog processor responsively to a predetermined number of counted fibrillatory signals to selectively activate said impedance analog processor, means for communicating impedance measurement of the ventricle to said impedance analog processor, means for communicating an impedance analog processor derived signal of a non-fibrillatory condition to said accumulator-control-logic means while the impedance analog processor is activated, said accumulator-control-logic means being thereafter simultaneously responsive to both ECG analog processor and impedance analog processor signals, and an energy delivery system responsive to said accumulator-control-logic means to effect a defibrillating electrical shock to the heart appropriate to the correction of a fibrillatory heart condition.

2. The automatic cardiac ventricular defibrillator in accordance with claim 1, where the means for sensing electrical and mechanical activity comprises spaced ventricular electrodes for providing a first signal in the form of an ECG analog signal and a second signal in the form of an impedance analog signal whereby both the electrical and the mechanical activities of the ventricle are monitored.

3. The automatic cardiac ventricular defibrillator in accordance with claim 2, including a catheter supporting said electrodes and receivable within the ventricle.

4. The automatic cardiac ventricular defibrillator in accordance with claim 1, wherein said impedance analog processor is effective when said accumulator-control-logic means receives a predetermined number of fibrillatory ECG signals in sufficient predetermined pattern and number.

5. The automatic cardiac ventricular defibrillator in accordance with claim 1, including a preprogrammed means having a quantitative weighting factor assigned to the signals of said ECG analog processor and impedance analog processor whereby the respective signals are made correspondent to said weighting factor before a combination thereof is effective for communicating the energy delivery system to the heart for delivery of the defibrillating electrical shock.

6. The automatic cardiac ventricular defibrillator in accordance with claim 1, in which said accumulator-control-logic means effects a preprogrammed pattern representative of ventricular fibrillation and forming a standard against which the processed signals of the ECG analog processor are compared to identify changes indicative of fibrillation and for additionally detecting changes in impedance as a potential heart fibrillation condition, each of said processed signals to said accumulator-control-logic means providing information potentially confirming a fibrillatory ventricular condition when in accordance with a preprogrammed weighted decision imposed on said signals.

7. The automatic cardiac ventricular defibrillator in accordance with claim 1, wherein the accumulator-control-logic means includes control means and accumulator means for imposing a weighting factor and incrementing or decrementing whereby said accumulator means is effective for operation of said energy delivery system.

8. The automatic cardiac ventricular defibrillator in accordance with claim 1, wherein the accumulator-control-logic means includes a control means responsive independently to said ECG analog and impedance analog processor signals, and accumulator means responsive to said control means to be effective in accordance with fibrillatory activity for said control means and accumulator means to detect and respond to discrete patterns of signals.

9. The automatic cardiac ventricular defibrillator in accordance with claim 1, wherein the accumulator-control-logic means includes an accumulator means and means for effecting decrementing and incrementing of the signal values collected by said accumulator means in accordance with said impedance analog and ECG analog processed signals, and a decoding logic means for activating said impedance analog processor whereby the signals are accumulated in a predetermined weighted relationship to each other and the effecting of said defibrillatory electrical shock is in accordance with the respective signals.

10. The automatic cardiac ventricular defibrillator in accordance with claim 1, further comprising a third electrode for electrical connection to said energy delivery system, and a catheter, said means for sensing electrical and mechanical activity comprising a pair of spaced ventricular electrodes, said catheter supporting said spaced ventricular electrodes whereby said defibrillatory electrical shock is effected between the pair of spaced electrodes and the third electrode.

11. The automatic cardiac ventricular defibrillator in accordance with claim 1, said accumulator-control-logic means including an accumulator, a control member for receiving ECG and impedance related signals, a logic unit operatively connected to said accumulator, and a missing-pulse detector, said control member comprising means for incrementing and decrementing said accumulator in response to said signals, said missing-pulse detector monitoring said ECG analog processor signals to detect a non-fibrillatory condition and responsively acting through said control member to reset said accumulator.

12. The automatic cardiac ventricular defibrillator in accordance with claim 11, wherein said logic unit is responsive to said accumulator for inhibiting the operation of said missing-pulse detector after the accumulator increments to a predetermined level.

13. An apparatus for continuously monitoring heart activity and automatically effecting a defibrillatory shock under heart fibrillating conditions, comprising means for sensing electrical and mechanical activity of the heart and of a predetermined ventricular fibrillation condition, means for measuring the electrical activity of the heart responsively to said sensing means, means for accumulating said measured electrical activity, means for monitoring the mechanical activity of the heart and operatively connected to said accumulating means, said accumulating means responsive to information representing a predetermined ventricular fibrillatory condition communicated from said measuring means and for activating the means for monitoring the mechanical activity, and a delivery means responsive to said accumulator means for correcting ventricular fibrillation when said accumulating means receives mechanical and electrical activity information each independently but conjointly through respective incrementing and decrementing values confirming a ventricular fibrillatory condition.

14. An automatic heart defibrillator comprising: sensor means for detecting cardiac electrical and mechanical activity information, means for communicating in the form of electrical signals the cardiac electrical and mechanical activity information from said sensor means, an ECG analog processor for receiving the electrical cardiac activity information from said communicating means, an mechanical-impedance analog processor for receiving the mechanical cardiac activity information from said communicating means, accumulator-control-logic means receiving the output of said ECG analog processor and for counting cardiac signals from said ECG analog processor and for triggering a defibrillatory action at predetermined quantitative threshold values thereof, means for connecting said mechanical-impedance analog processor and said accumulator-control-logic means to furnish an input signal which decrements the counted value derived by said accumulator-control-logic means from the ECG analog processor, the total cardiac information accumulated being the combined independently derived information from said mechanical-impedance and ECG analog processors respectively, said accumulator-control-logic means including logic means for deactivating said mechanical-impedance processor.

15. The defibrillator in accordance with claim 14, in which said mechanical-impedance analog processor is normally deactivated, said logic means responsive to said accumulator-control-logic means at critical heart fibrillatory conditions transmitted by said ECG analog processor and effective to activate said mechanical-impedance analog processor whereby the ECG analog processor and mechanical-impedance processor thereafter perform conjointly and independently to monitor both electrical and mechanical heart activity information and each processor furnishing information to said accumulator-control-logic means which counts the fibrillatory heart activity derived from continuous monitoring by each of said processors.

16. A method for monitoring cardiac ventricular activity for detecting ventricular fibrillation, comprising the steps of continuously sensing the electrical activity of the heart, processing the sensed electrical information by an electrical monitoring means for detection of a predetermined pattern of ventricular fibrillation, operatively activating a mechanical monitoring means upon attainment of the predetermined pattern of ventricular fibrillation, and processing independently and conjointly signals derived from said electrical and mechanical monitoring means whereby upon their conjoint signalling of ventricular fibrillation, through respective incrementing and decrementing values, defibrillatory corrective action is effected.

17. The method in accordance with claim 16, further comprising the steps of weighting the signals respectively generated by the electrical and mechanical monitoring means whereby the weighted signals attain an accumulated value in accordance with the proportions of the respectively weighted signals, and in accordance with said accumulated value thereafter delivering a defibrillating ventricular shock.

18. The method of claim 16, including the step of analyzing the electrical activity of the heart through a missing-pulse detector circuit and suppressing defibrillating operation when the missing-pulse detector circuit detects a non-fibrillating ventricular condition.

19. The method in accordance with claim 16, including the step of positioning ventricular electrode means and thereafter sensing the electrical and mechanical activity of the ventricle.

20. The method in accordance with claim 16, including the steps of incrementing or decrementing an accumulator storage count as derived from the electrical and mechanical monitoring means to detect a pattern of heart activity and to evaluate the predominate presence or predominate absence of ventricular fibrillation, and generating a signal to inhibit decrementing operation at a predetermined accumulated storage count.

21. A method of monitoring cardiac activity and applying a ventricular defibrillation action upon sensing and confirming the existence of a fibrillatory condition, comprising the steps of: continuously monitoring the electrical activity of the heart for the presence of a predetermined pattern of fibrillatory heart activity, independently activating a second monitoring means which is responsive to the mechanical activity of the heart and which monitors a second and independent set of criteria received from the ventricle and related to the stroke volume of the ventricle, and thereafter independently and conjointly monitoring the heart and delivering a defibrillatory action upon concurrent and jointly verified fibrillatory activity of a predetermined pattern and extent, determined through respective incrementing and decrementing values.

22. A method for monitoring cardiac ventricular activity for detecting ventricular fibrillation, comprising the steps of: supplying simultaneously to a monitoring means signals of electrical and mechanical activity of the ventricle, and weighting the respective signals by which there is determined a fibrillatory condition and in accordance with a predetermined formula whereby the condition of fibrillation is conjointly verified through respective incrementing and decrementing values by both such signals, and delivering a defibrillating action in response to the conjoint verification by such signals.

23. A method for monitoring cardiac ventricular activity for detecting ventricular fibrillation, comprising the steps of sensing the electrical and mechanical activity of the heart, processing the sensed electrical and mechanical activity for detection of a predetermined pattern of ventricular fibrillation, weighting the signals respectively generated from the electrical and mechanical activity whereby the weighted signals enhance the accuracy in determining the presence of ventricular fibrillation, and conjointly processing through incrementing and decrementing values the weighted signals to determine the presence of ventricular fibrillation, and thereafter delivering a defibrillatory action.

* * * * *